United States Patent
Wang et al.

(10) Patent No.: US 10,092,382 B2
(45) Date of Patent: Oct. 9, 2018

(54) PROPHY ANGLE DEVICE AND METHOD OF USE

(71) Applicants: CROSSTEX INTERNATIONAL, INC., Hauppauge, NY (US); PAC-DENT INTERNATIONAL, INC., Walnut, CA (US)

(72) Inventors: Daniel Wang, Rowland Heights, CA (US); Denghui Chen, Suzhou (CN); Bo Tao, Chino, CA (US); Bo Yue, Suzhou (CN); Yong Zhu, Suzhou (CN)

(73) Assignees: Crosstex International, Inc., Hauppauge, NY (US); Pac-Dent International, Inc., Walnut, CA (US)

( * ) Notice: Subject to any disclaimer, the term of this patent is extended or adjusted under 35 U.S.C. 154(b) by 26 days.

(21) Appl. No.: 15/327,891

(22) PCT Filed: Jul. 24, 2014

(86) PCT No.: PCT/US2014/048045
§ 371 (c)(1),
(2) Date: Jan. 20, 2017

(87) PCT Pub. No.: WO2016/014065
PCT Pub. Date: Jan. 28, 2016

(65) Prior Publication Data
US 2017/0202652 A1    Jul. 20, 2017

(51) Int. Cl.
*A61C 17/32* (2006.01)
*A61C 1/12* (2006.01)
*A61C 17/00* (2006.01)
(Continued)

(52) U.S. Cl.
CPC ........... *A61C 17/32* (2013.01); *A61C 1/12* (2013.01); *A61C 1/141* (2013.01); *A61C 1/144* (2013.01); *A61C 17/005* (2013.01); *A61D 5/00* (2013.01)

(58) Field of Classification Search
CPC ....... A61C 17/3409; A61C 17/32; A61C 1/12; A61C 1/141; A61C 1/144; A61C 17/05; A61D 5/00
See application file for complete search history.

(56) References Cited

U.S. PATENT DOCUMENTS

| 3,740,853 A | * | 6/1973 | Brahler | ............... A61C 17/005 |
| | | | | 433/112 |
| 3,869,877 A | * | 3/1975 | Brahler | ............... A61C 17/005 |
| | | | | 433/112 |

(Continued)

FOREIGN PATENT DOCUMENTS

| GB | 2212570 A | 7/1989 |
| WO | 2005004746 A1 | 1/2005 |

OTHER PUBLICATIONS

International Search Report and Written Opinion of the International Searching Authority dated Dec. 11, 2014 of International Application No. PCT/US2014/048045 filed on Jul. 24, 2014, entire document.

*Primary Examiner* — Nicholas Lucchesi
(74) *Attorney, Agent, or Firm* — William D. Schmidt, Esq.; Sorell, Lenna & Schmidt LLP

(57) ABSTRACT

A disposable prophy angle is provided, the prophy angle comprising a housing containing a drive shaft and a driven shaft; the drive shaft having a proximal end and a distal end and a longitudinal axis therebetween, the distal end having a substantially conical driving portion and a projection, the proximal end of the drive shaft configured to engage a dental hand piece; and the driven shaft having a driven portion comprising a recess configured for engagement by the projection and/or the substantially conical portion of the drive shaft to oscillate the driven shaft at an oscillation angle greater than 90 degrees. In some embodiments, there is a method of making a disposable prophy angle by overmold- (Continued)

ing a prophy cup to the prophy angle. In other embodiments, there is a method of using the prophy angle to prevent tooth decay.

29 Claims, 7 Drawing Sheets

(51) Int. Cl.
*A61C 1/14* (2006.01)
*A61D 5/00* (2006.01)

(56) References Cited

U.S. PATENT DOCUMENTS

| | | | | |
|---|---|---|---|---|
| 5,380,202 | A * | 1/1995 | Brahler | A61C 17/005 433/166 |
| 5,433,605 | A * | 7/1995 | Strobl, Jr. | A61C 17/005 433/112 |
| 5,529,495 | A * | 6/1996 | Edwards | A61C 1/18 433/112 |
| 5,531,599 | A * | 7/1996 | Bailey | A61C 17/005 433/125 |
| 5,784,743 | A | 7/1998 | Shek | |
| 5,931,672 | A | 8/1999 | Postal et al. | |
| 6,053,732 | A * | 4/2000 | Sale | A61C 17/005 433/125 |
| 6,247,931 | B1 | 6/2001 | Postal et al. | |
| 6,409,507 | B1 | 6/2002 | Postal et al. | |
| 6,848,451 | B2 | 2/2005 | Postal et al. | |
| 7,955,079 | B2 | 6/2011 | Chronister et al. | |
| 2006/0210948 | A1 | 9/2006 | Rose et al. | |
| 2010/0035205 | A1 | 2/2010 | Wang et al. | |

\* cited by examiner

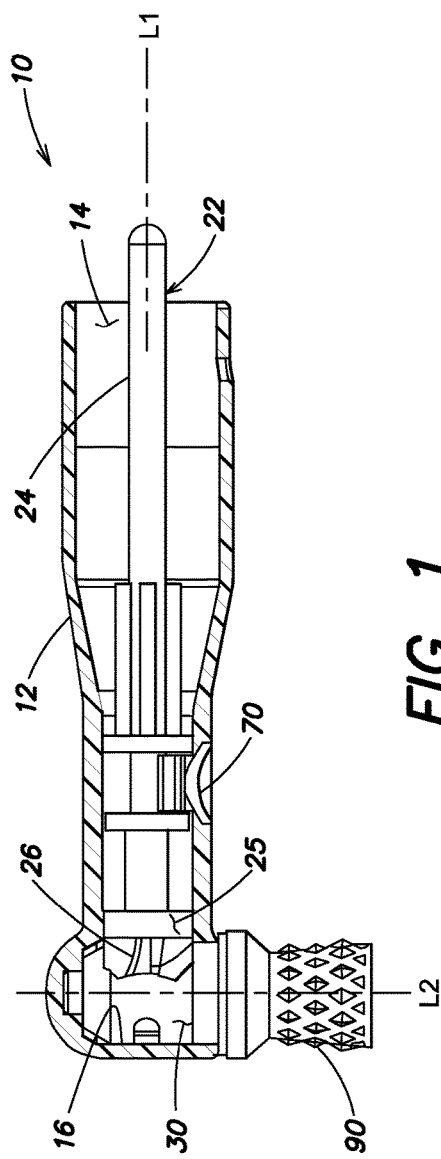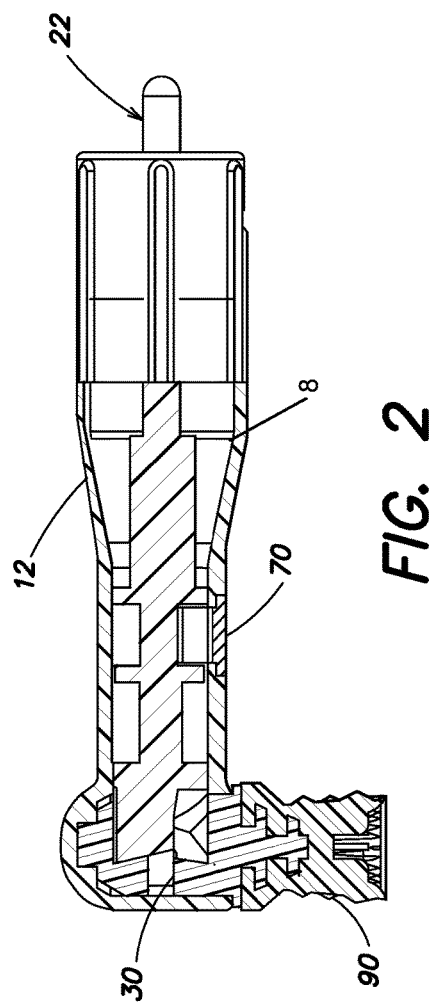

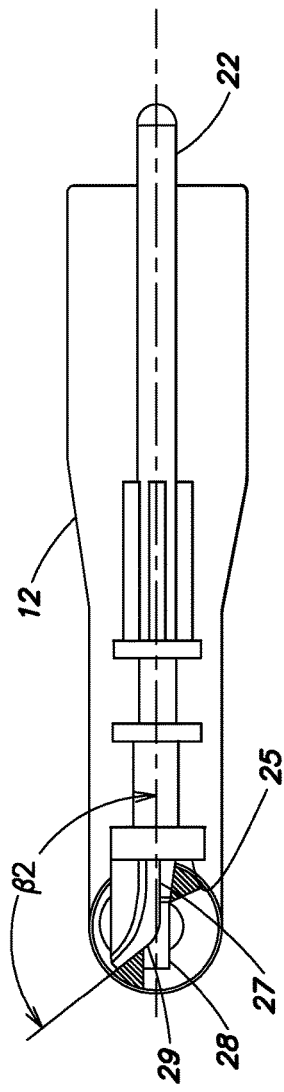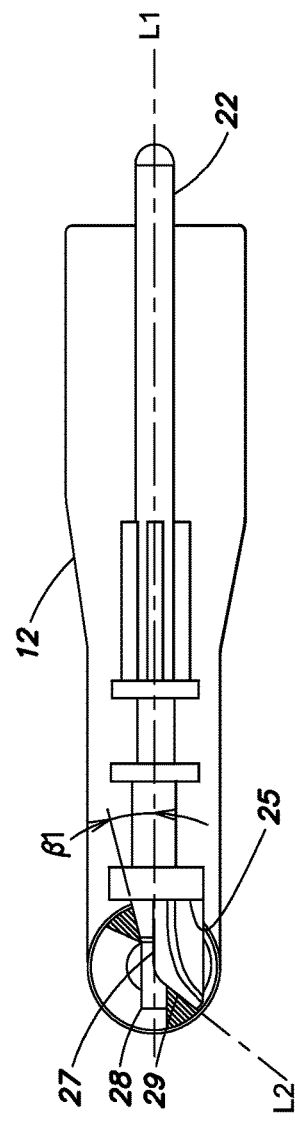

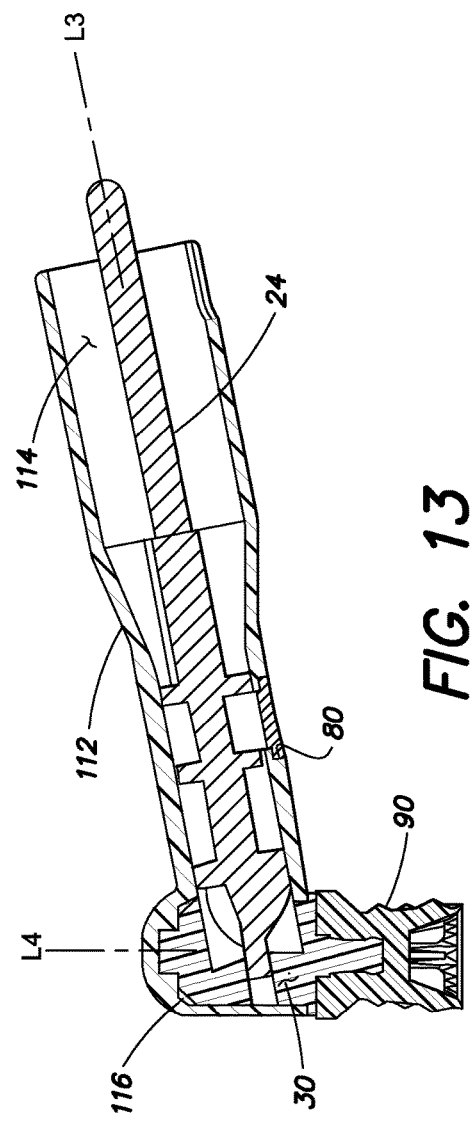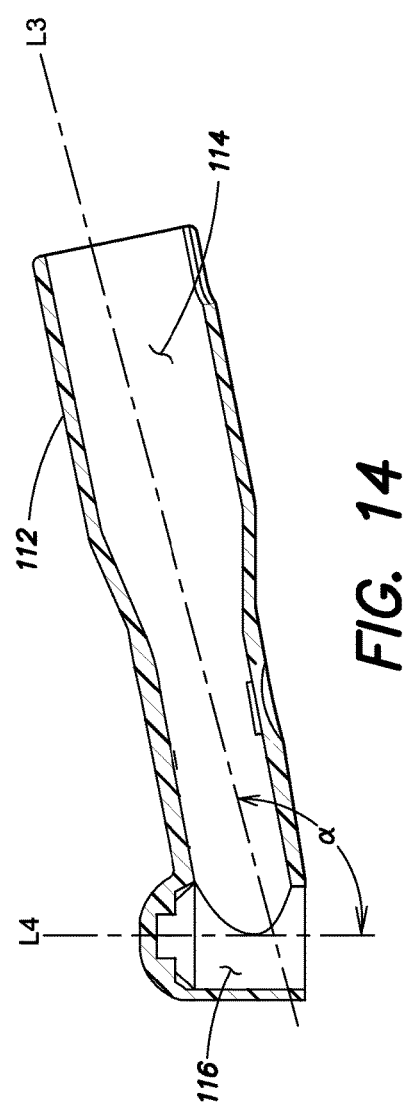
FIG. 13
FIG. 14

PROPHY ANGLE DEVICE AND METHOD OF USE

BACKGROUND

Today, dental and veterinary professionals use dental instruments commonly known as dental prophylaxis (prophy) angles attached to prophy cups for cleaning and polishing teeth. The prophy cup, which is filled with dental paste, is pressed against the tooth surfaces to clean and polish the teeth. Different prophy pastes can be used depending upon the dental health of the patient and amount of dental plaque and calculus that needs to be removed. For example, NUPRO® prophylaxis paste, available from Dentsply International (York, Pa.) can be used as the prophy paste, and this paste is available in different textures (fine, medium, and coarse) depending upon the size of the abrasive particles used in the paste. Fluoride-containing and fluoride-free prophy pastes are also available. A professional cleaning with prophy paste helps prevent dental caries caused by bacteria in dental plaque. Bacteria produce acids that eat into the tooth eventually causing cavities to form therein.

When the teeth are cleaned and polished by a dental or veterinary professional, the dental plaque can be effectively removed from the tooth surfaces of the patient. In addition, calculus build-up and extrinsic stains caused by beverages and food can also be effectively removed. The prophy angles are normally made from an inexpensive, flexible plastic and the prophy cup is made from a rubbery material. Many of the prophy angles available today are for single use and are disposed of after one-time use.

Conventional dental prophy angles are generally effective; however, they have some drawbacks. For example, conventional prophy angles and prophy cups when they are filled with dental paste and attached to the prophy angles are in a constant one-directional rotational motion during use, which causes excessive dental paste splatter when the prophy cup contacts the surface of the tooth. This splatter is not only messy but also can lead to misapplication of the dental paste to the tooth surface.

Conventional prophy angles operate at one speed instead of variable speeds, which also can lead to the excessive dental paste splatter. The prophy cup in a conventional prophy angle is a separate part of the prophy angle assembly and not directly attached to the driven shaft. Because of this design, relative rotational motion between the prophy cup and the driven shaft are associated with excessive heat generation, which causes the prophy angle to wear out during use or need replacement. Some conventional prophy angles have reduced oscillation angles due to the design of drive gear and driven gear, and orthogonal gear connection facilitates an uncomfortable wrist position for the dental or veterinary professional during use.

Therefore, there is a need in the dental and veterinary industry for a prophy angle which improves polishing efficiency by reducing the downtime caused by excessive heat during procedures, allows for variable operating speeds to cut down paste splatter, increases the oscillation angle, and utilizes a non-orthogonal gear to ergonomically correct the user's neutral wrist position to allow the user to operate the device with less strain on their hand.

SUMMARY

The prophy angles and methods of the present disclosure improve polishing efficiency by reducing the downtime caused by excessive heat during procedures, allow for variable operating speeds to cut down paste splatter, increase the oscillation angle, and utilize a non-orthogonal gear to ergonomically correct the user's neutral wrist position to allow the user to operate the device with less strain on their hand.

In one embodiment, there is a disposable prophy angle comprising a housing containing a drive shaft and a driven shaft; the drive shaft having a proximal end and a distal end and a longitudinal axis therebetween, the distal end having a substantially conical driving portion and a projection, the proximal end of the drive shaft configured to engage a dental hand piece; and the driven shaft having a driven portion comprising a recess configured for engagement by the projection and/or the substantially conical portion of the drive shaft to oscillate the driven shaft at an oscillation angle greater than 90 degrees.

In one embodiment, the prophy angle device includes an engagement mechanism between the driven gear and the drive gear creating an oscillating motion at variable speeds throughout each revolution of the drive gear. This configuration reduces the resulting centrifugal forces exerted on the prophylaxis paste when compared to traditional prophylaxis cups' constant one-directional rotational motion, thus keeping more prophylaxis paste inside the prophylaxis cup during use. This configuration improves the polishing efficiency and reduces splatter which ultimately improves patient experience.

In various embodiments, there is a disposable prophy angle comprising a housing containing a drive shaft and a driven shaft; the drive shaft having a proximal end and a distal end and a longitudinal axis therebetween, the distal end having a substantially conical driving portion and a projection extending along the longitudinal axis of the driving portion, the proximal end of the drive shaft configured to engage a dental hand piece; the driven shaft having a driven portion comprising a recess configured for engagement by the projection and/or the substantially conical portion of the drive shaft so as to oscillate the driven shaft at an oscillation angle of about 120 degrees; and a prophy cup contacting the driven shaft to oscillate with the driven shaft.

In yet another embodiment, there is a disposable prophy angle comprising a housing containing a drive shaft and a driven shaft; the drive shaft having a proximal end and a distal end and a longitudinal axis therebetween, the distal end having a substantially conical driving portion and a projection extending along the longitudinal axis of the driving portion, the proximal end of the drive shaft configured to engage a dental hand piece; the driven shaft having a driven portion comprising a recess configured for engagement by the projection and/or substantially conical portion of the drive shaft so as to oscillate the driven shaft at an oscillation angle of about 120 degrees; and a prophy cup contacting the driven shaft to oscillate with the driven shaft, wherein the drive shaft is disposed at an angle of about 96 degrees to about 120 degrees relative to the driven shaft.

In one embodiment, the prophy angle device reduces heat build-up on a patient's teeth surface during polishing procedures by overmolding the prophylaxis cup directly onto the driven gear. This configuration removes the relative rotational motion and associated heat generation between the driven gear and prophylaxis cup. In one embodiment, this configuration reduces heat from contact friction between the prophylaxis cup and the teeth. In one embodiment, this configuration improves polishing efficiency by reducing the downtime caused by excessive heat during procedures.

In one embodiment, a disposable prophy angle is provided comprising a housing containing a drive shaft and a driven shaft. The drive shaft having a proximal end and a distal end and a longitudinal axis therebetween. The distal end has a substantially conical driving portion and a projection. The proximal end of the drive shaft is configured to engage a dental hand piece. The driven shaft has a driven portion comprising a recess configured for engagement by the projection and/or the substantially conical portion of the drive shaft to oscillate the driven shaft at an oscillation angle greater than 90 degrees to about 120 degrees. The disposable prophy angle is a contra angle and a prophy cup is attached to the driven shaft by overmolding.

In an exemplary embodiment, there is a method of making a disposable prophy angle, the method comprising overmolding a prophy cup to a driven shaft of a housing, the housing containing a drive shaft and the driven shaft; the drive shaft having a proximal end and a distal end and a longitudinal axis therebetween, the distal end having a substantially conical driving portion and a projection, the proximal end of the drive shaft configured to engage a dental hand piece; and the driven shaft having a driven portion comprising a recess configured for engagement by the projection and/or the substantially conical portion of the drive shaft to oscillate the driven shaft at an oscillation angle greater than 90 degrees.

In yet another exemplary embodiment, there is a method of applying a dental composition to a tooth structure, the method comprising applying a dental paste in a prophy cup to the tooth structure, the prophy cup attached to a driven shaft of a housing, the housing containing a drive shaft and the driven shaft; the drive shaft having a proximal end and a distal end and a longitudinal axis therebetween, the distal end having a substantially conical driving portion and a projection, the proximal end of the drive shaft configured to engage a dental hand piece; and the driven shaft having a driven portion comprising a recess configured for engagement by the projection and/or the substantially conical portion of the drive shaft to oscillate the driven shaft at an oscillation angle greater than 90 degrees.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 1 illustrates a side cross-section view of an embodiment of a prophy angle dental device;

FIG. 2 a side cross-section view of an embodiment of a prophy angle dental device;

FIG. 7 illustrates a side cross-section view of a prophy angle dental device;

FIG. 8 illustrates a side cross-section view of a prophy angle dental device;

FIG. 13 illustrates a perspective view of an embodiment of a housing of a prophy angle dental device; and FIG. 14 illustrates a side view of an embodiment of a driven shaft of a prophy angle dental device.

Figure 3:
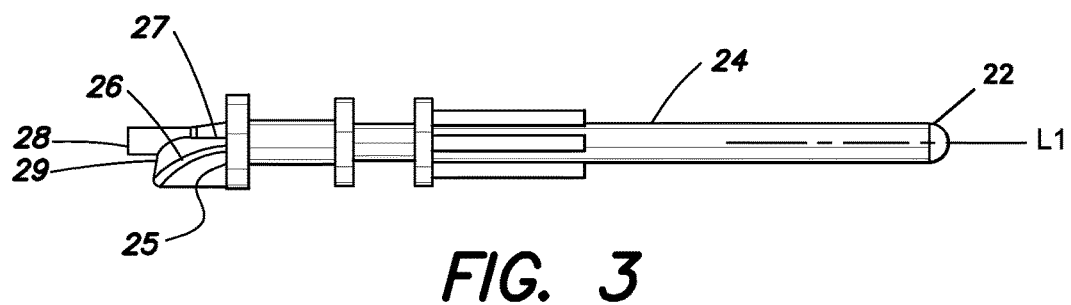
FIG. 3 illustrates a side view of a drive shaft of the prophy angle dental device.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a rib" includes one, two, three or more ribs.

Reference will now be made in detail to certain embodiments of the disclosure, examples of which are illustrated in the accompanying drawings. While the disclosure will be described in conjunction with the illustrated embodiments, it will be understood that they are not intended to limit the disclosure to those embodiments. On the contrary, the disclosure is intended to cover all alternatives, modifications, and equivalents, which may be included within the disclosure as defined by the appended claims.

The prophy angles and methods of the present disclosure improve polishing efficiency by reducing the downtime caused by excessive heat during procedures, allow for variable operating speeds to cut down paste splatter, increase the oscillation angle, and utilize a non-orthogonal gear to ergonomically correct the user's neutral wrist position to allow the user to operate the device with less strain on their hand.

In one embodiment, there is a disposable prophy angle comprising a housing containing a drive shaft and a driven shaft; the drive shaft having a proximal end and a distal end and a longitudinal axis therebetween, the distal end having a substantially conical driving portion and a projection, the proximal end of the drive shaft configured to engage a dental hand piece; and the driven shaft having a driven portion comprising a recess configured for engagement by the projection and/or the substantially conical portion of the drive shaft to oscillate the driven shaft at an oscillation angle greater than 90 degrees.

As shown in FIGS. 1 and 2, a disposable prophy angle 10 includes a housing 12 that contains the drive shaft 24 and the driven shaft 30. Housing 12 includes a first cavity 14 and a second cavity 16. First cavity 14 defines a longitudinal axis L1. Second cavity 16 defines a second longitudinal axis L2 disposed transverse to axis L1 of first cavity 14. Cavity 14 is configured for disposal of a drive shaft 24. The driven shaft has a drive shaft end 22 configured to be coupled to a dental hand piece that engages the drive shaft end 22 and provides the rotary motion and torque to rotate the drive shaft for use of the prophy angle. These dental hand pieces are available from various manufactures. The drive shaft 24 engages the driven shaft 30 and oscillates the prophy cup 90 in a reciprocating motion so that the prophy cup oscillates back and forth at an angle of about 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 degrees. The drive shaft 24 engages the driven shaft 30 such that there is continuous contact during rotation of the driven shaft. Because of the shapes of the drive shaft and the driven shaft, rotation of the drive shaft causes oscillatory rotation of the driven shaft. Rotation of the drive shaft thus imparts an oscillatory rotation to the driven shaft. This reduces splatter of any dental paste disposed in the prophy cup.

In some embodiments, the housing 12 can have a plurality of supports 8 transverse to the housing that reduce or prevent unwanted lateral movement of the drive shaft. These supports 8 can be disposed on discrete portions of the interior surface of the housing and run along the housing's longitudinal axis to prevent or reduce unwanted lateral movement of the drive shaft so that noise from movement of the gears is reduced.

The prophy angle including the prophy cup and its component parts (e.g., drive shaft, driven shaft, housing, etc.) may be made of any polymeric material. Examples of polymeric materials can include polyethylene, polypropylene, polybutylene, polystyrene, polyester, acrylic polymers, polyvinylchloride, polyamide, polycarbonate, polyetherimide like ULTEM or the like; polymeric alloys such as Xenoy resin, which is a composite of polycarbonate and polybutyleneterephthalate or Lexan plastic, which is a copolymer of polycarbonate and isophthalate terephthalate resorcinol resin (all available from GE Plastics) are also suitable; liquid crystal polymers, such as an aromatic polyester or an aromatic polyester amide containing, as a constituent, at least one compound selected from the group consisting of an aromatic hydroxycarboxylic acid (such as hydroxybenzoate (rigid monomer), hydroxynaphthoate (flexible monomer), an aromatic hydroxyamine and an aromatic diamine, polyesteramide anhydrides with terminal anhydride group or lateral anhydrides or combinations thereof; or biocompatible or biodegradable polymers including polyester material such as polylactic acid resin (comprising L-lactic acid and D-lactic acid); polyhydroxyvalerate/hydroxybutyrate resin (copolymer of 3-hydroxybutyric acid and 3-hydroxypentanoic acid (3-hydroxyvaleric acid) (PHBV) and polyhydroxyalkanoate (PHA) copolymers; polyester/urethane resin; other biocompatible polymers such as Polysulfone, PPS (polyphenylene sulfide), PEEK (polyetheretherketone) or the like are also suitable.

In some embodiments, the prophy cup or brush can be overmolded to the driven shaft. The term "overmolding" as used herein refers to a molding process in which two or more polymer materials (e.g., polymer materials for the driven shaft and prophy cup) are combined to produce a single part. In some embodiments, the driven shaft containing a rigid polymer seamlessly binds a rubber-like elastomer of the prophy cup so that the driven shaft and the prophy cup are monolithic and one single piece.

In some embodiments, overmolding includes molding the cup around or onto a pre-formed gear (e.g., driven shaft). In one embodiment, this configuration reduces heat from contact friction between the prophylaxis cup and the teeth. In some embodiments, during molding of the cup, parts of the gear come in contact with the material forming the cup and may become softened or slightly melted, causing a co-mingling of the materials to form a stronger bond. In some embodiments, the material used in constructing the cup seeps through the cup and serves as an additional anchor that strengthens the attachment forces between the cup and the gear. In various embodiments, a method of overmolding is provided, the method comprises a first polymer and then applying a second polymer by injection molding (e.g., by a two-color injection molding process). In some embodiments, overmolding can include more than one overmolding operation to form part or the entire device using more than two polymers and/or with more than two layers, if desired.

In some embodiments, the cup and gear, and/or other parts of the device may be molded via co-injection, overmolding and/or insert-molding systems. Overmolding materials that may be used include urethanes, styrene-ethylene-butylene-styrene or SEBS elastomers (e.g. Kraton or Dynaflex, available from GLS Corporation of Cary, Ill., and metallocene elastomers (e.g., Engage, available from DuPont Dow Elastomers, L.L.C. of Freeport, Tex.) and fully vulcanized ethylene-propylene-diene-monomers in a continuous matrix of polypropylene (e.g., Santoprene, available from Advanced Elastomer Systems, L.P., of Akron, Ohio). In some embodiments, the elastomer has a Shore A hardness of less than about 60, and preferably a Shore A hardness in the range of about 5-45. In some embodiments, the elastomer has a Shore A hardness of about 40.

The prophy cup or brush that is attached to the driven shaft can be used to apply prophy or dental paste to the tooth. The prophy or dental paste can contain an abrasive, a binder, and a liquefying agent which is used to create a flow of the paste. The prophy cup functions by carrying the prophy paste to the surface of the teeth and the cup material polishes surfaces of the teeth, including subgingival and interproximal surfaces. Typically the prophy cup picks up the paste by dipping the cup in a reservoir of paste.

As the cup is rotated and oscillates back and forth by the prophy angle, the prophy paste exits the cavity and is applied to the tooth. The paste acts as both a lubricant and an abrasive which removes stains, plaque, and calculus build-up, and the paste can clean and polish the teeth.

The prophy cup acts as a reservoir which holds prophy paste to be applied to the tooth; it distributes the paste to a working surface of the cup to clean and polish teeth; and it cleans and polishes surfaces of the teeth, including subgingival and interproximal surfaces of the teeth. Prophy cups typically form a well or cavity into which the paste is inserted, as by dipping the cup in a reservoir of paste. As the cup is rotated by a driven shaft, the paste exits the cavity and is applied to the tooth.

Different prophy pastes can be used depending upon the dental health of the patient or animal and amount of dental plaque and calculus that needs to be removed. For example, NUPRO® prophylaxis paste, available from Dentsply International (York, Pa.) can be used as the prophy paste, and this paste is available in different textures (fine, medium, and coarse) depending upon the size of the abrasive particles used in the paste. Fluoride-containing and fluoride-free prophy pastes are available.

In some embodiments, the housing 12 of the prophy angle 10 comprises a lock 70 disposed adjacent to the drive shaft 24 that is movable in a locking position shown in FIG. 1. The lock engages a region of the drive shaft 24 and prevents rotation of it. In this way, oscillation of the driven shaft 30 and the prophy cup 90 will be prevented. In various embodiments, the lock can have indicator markings (e.g., numbers, lines, letters, color markers, etc.) to indicate that the prophy angle is locked and will not rotate or unlocked and, therefore, will rotate.

In some embodiments, the housing comprises a lock 70 disposed adjacent to the drive shaft 24 that is movable in a unlocked position shown in FIG. 2. The lock engages the housing but does not engage the drive shaft and does not prevent rotation of it. In this way, oscillation of the driven shaft 30 and the prophy cup 90 can occur when the drive shaft end 22 of the prophy angle is coupled to a dental hand piece and the motor is turned on.

Figure 4:
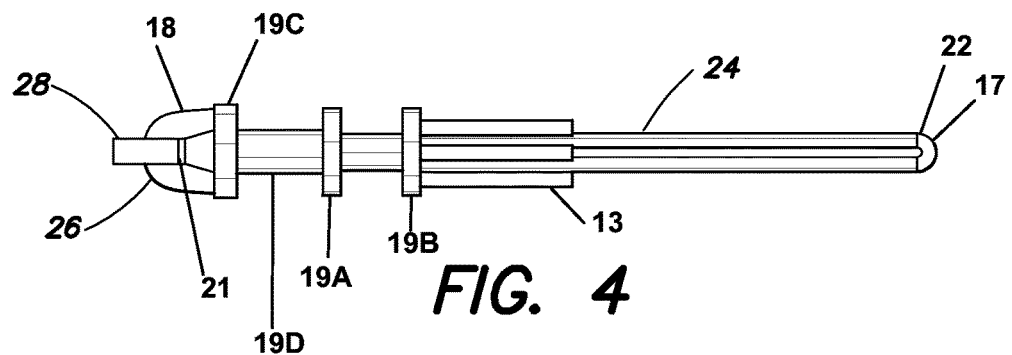
FIG. 4 illustrates a side view of a drive shaft of the prophy angle dental device.

As shown in FIGS. 3 and 4, drive shaft end 22 includes a drive shaft 24, a base portion 25 and a cam surface 26. The drive shaft 24 runs longitudinally in the housing and has proximal end 17 that is configured to engage a dental hand piece that provides the rotary motion to rotate the drive shaft 24.

The drive shaft 24 comprises distal end 18 having surface 26 that includes a planar portion 27 and a conical portion 29 in communication with planar portion 27. The planar portion comprises a projection 28 that extends beyond conical portion 29. The projection 28, the conical portion 29, and the surface 26 of the conical portion 29 engage cavity 61 of the driven shaft 30 to cause oscillating motion that allows prophy cup to move in a back and forth motion at an angle of about 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 degrees relative to the drive shaft 24.

Conical portion 29 forms an angle with axis L1 as shown in FIGS. 7 and 8. Conical portion 29 forms an acute angle β1 for part of the rotation relative to the interaction of the drive shaft 24 to the driven shaft 30 particularly the conical portion when the conical portion 29 is facing in a downward direction. An obtuse angle of β2 is shown for rotation of the driven shaft 30 particularly the conical portion when the conical portion 29 is facing in a upward direction that causes the oscillation movement of the prophy cup.

The driving portion includes a flange, such as, for example, a projection 28 extending from the base portion and disposed along axis L1 of the drive shaft. In some embodiments, projection 28 can extend in various orientations, such as, for example, series, parallel, offset or staggered. Projection 28 extends past a top surface of conical portion 29 for engagement with the driven shaft, as discussed herein. The projection is disposed above conical portion 29.

To facilitate oscillation, in some embodiments, the drive shaft can include a plurality of rings shown as 19A, 19B, and 19C that are disposed around the diameter 19D. The plurality of rings makes the rotational movement of the drive shaft 24 easier in the housing. The diameter 19D of the drive shaft 24 increases as the distal end 18 of drive shaft is approached. The conical portion 29 can have a ring 19C disposed at its base to ease rotation of the drive shaft.

The drive shaft 24, in some embodiments, can have a plurality of ribs 13 that run a long a portion of the longitudinal axis L1 of the drive shaft. These can be disposed about the diameter of the drive shaft 24 and provide support and balance to the drive shaft that aid in rotation. In some embodiments, the plurality of ribs 13 can be transverse to one or more rings (e.g., 19C) of the drive shaft 24, which will also provide for additional support and balance to the drive shaft that aids in rotation of the drive shaft.

In some embodiments, the drive shaft includes a groove 21 disposed along axis L1 of the drive shaft. The positioning of groove 21 along axis L1 facilitates an increase in oscillation angle of a prophy cup. The addition of groove 21 prevents the driven shaft from interfering with a distal end on the driving portion during its oscillation, allowing the oscillation angle to be greater than 90 degrees, such as, for example, an oscillation angle of 91 to 180 angle degrees.

In one embodiment, the oscillation angle is about 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179 and/or 180 degrees. In one embodiment, the oscillation angle is 120 degrees.

In one embodiment, the design of the drive shaft and the driven gear increases the oscillating angle from 90 degrees to 120 degrees, which creates a non-constant oscillating motion at variable speeds throughout each revolution of the drive shaft which reduces the resulting centrifugal forces exerted on the prophy paste. In some embodiments, the increase in the oscillation angle is achieved by including a groove along a central axis of the drive shaft having a smaller diameter than the distal end of the drive shaft. In some embodiments, the oscillation angle is increased by the configuration of the distal end and a top section on the drive shaft.

In some embodiments, the addition of the groove prevents the driven shaft from interfering with the distal end of the drive shaft during oscillation thereby facilitating an oscillation angle greater than 90 degrees. Without the groove, the maximum oscillation angle for the driven gear is limited to 90 degrees. In some embodiments, the design of the distal end of the drive shaft effectively drives the oscillation motion of the driven shaft.

Figure 5:
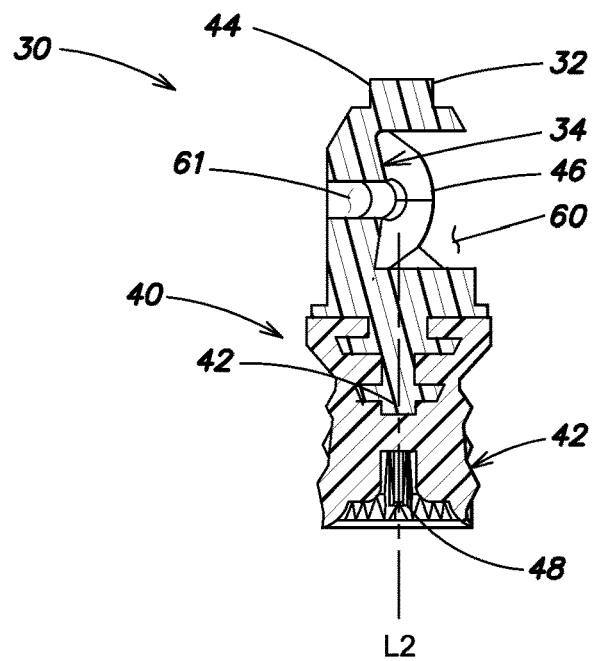
FIG. 5 illustrates a side cross-section view of a driven portion of a prophy angle dental device.
Figure 6:
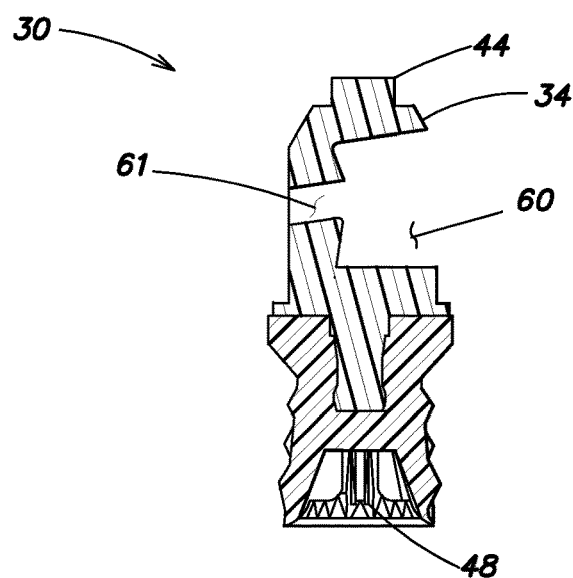
FIG. 6 illustrates a side cross-section view of a driven portion of a prophy angle dental device.

FIGS. 5-6 illustrate the driven shaft 30 that is engaged by the drive shaft. More particularly, projection 28, the conical portion 29, and the surface 26 of the conical portion 29 engage cavity 61 of the driven shaft 30 to cause oscillating motion that allows the prophy cup to move in a back and forth motion at an angle of about 90 to about 120 degrees relative to the drive shaft 24. Due to this design, there is improved polishing efficiency by allowing for variable operating speeds and increase in the oscillation angle to reduce paste splatter from the prophy cup. In one embodiment, this configuration reduces heat from contact friction between the prophylaxis cup and the teeth. Further, the disposable prophy angle provided reduces heat from contact friction between the driving shaft and the driven shaft by allowing back and forth motion at an angle of about 90 to about 120 degrees relative to the drive shaft 24.

Cavity 61 is configured to receive at least projection 28 and allows rotation of the driven shaft 30 about the projection 28. Driven shaft 30 includes a ridge 32 and a driven portion 34 configured for engagement with a drive shaft. Driven shaft 30 includes a driven rotor 40 including a rotor head 42, a rotor neck 44, a cam surface 46, a cup flange 48, and a cup holder 50. Cam surface 46 of driven portion 34 includes a cavity 60, and a cavity 61 in communication with cavity 60. Cavity 60 is configured for disposal of conical portion 29 of the drive shaft. Cavity 60 includes a shape complimentary to conical portion 29 that allows the drive shaft to engage the driven shaft snuggly allowing conical portion 29 to rotate freely within cavity 60. Cavity 61 is configured to receive projection 28 and engage it snuggly. As the driving portion is rotated, conical portion 29 engages cavity 60 causing driven portion 34 to oscillate the prophy cup back and forth.

The drive shaft 24 and driven shaft 30 have driving surfaces that are shaped to inter-engage each other, resulting in a camming action that translates rotation of drive shaft 24 into oscillatory rotation of driven shaft 30 substantially without play between the driving surfaces. The planar portion of the driving mechanism extends substantially parallel with axis L1. In some embodiments, conical portion 29 extends at a 45 degree angle or less (e.g., 44, 43, 42, 41, 40, 39, 38, 37, 36, 35, 34, 33, 32, 31, 30, 29, 28, etc.) along axis L2 with respect to rotation axis L1, as shown in FIG. 8. Projection 28 of the driven surface is aligned with rotation axis L1, facilitating alignment of planar surface 27 with axis L1.

Driven shaft 30 causes drive shaft 24 to oscillate a variable speeds. In some embodiments, driven shaft 30 causes drive shaft 24 to oscillate at variable speeds of approximately 2500 to 6000 rpm. In some embodiments, drive shaft 24 oscillates at about 2500, 2505, 2510, 2515, 2520, 2525, 2530, 2535, 2540, 2545, 2550, 2555, 2560, 2565, 2570, 2575, 2580, 2585, 2590, 2595, 3000, 3005, 3010, 3015, 3020, 3025, 3030, 3035, 3040, 3045, 3050, 3055, 3060, 3065, 3070, 3075, 3080, 3085, 3090, 3095, 4000, 4005, 4010, 4015, 4020, 4025, 4030, 4035, 4040, 4045, 4050, 4055, 4060, 4065, 4070, 4075, 4080, 4085, 4090, 4095, 5000, 5005, 5010, 5015, 5020, 5025, 5030, 5035, 5040, 5045, 5050, 5055, 5060, 5065, 5070, 5075, 5080, 5085, 5090, 5095 and/or 6000 rpm. Varying the oscillation speeds facilitates reduction of the resulting centrifugal forces exerted on the prophy paste when compared to prior art constant one-directional rotational motion. The result is maintaining more prophy paste inside the prophy cup during use, improvement of the polishing efficiency, reduction of splatter which ultimately improves patient experience.

In one embodiment, the cam action of the drive shaft 24 and the driven rotor 40 include matching cam surfaces. In some embodiments, the surface matched rotors couple together via an engagement at an acute angle formed between the cam surface 46 on the drive shaft 24 and a matching hill end of the driven rotor axis. In some embodiments, an axis of the drive shaft and an axis of the driven rotor form an obtuse angle (e.g., more than 90 degrees but less than 180 degrees).

In one embodiment, the housing of the prophy angle includes a longitudinal and a transverse section in one integral piece. In some embodiments, the drive shaft comprises a lock that couples the drive shaft in the longitudinal section of the housing to the driven shaft, more particularly the rotor in the transverse section of the housing, via the non-orthogonal gear connection between the drive shaft axis and the rotor axis, which maintains continuous engagement of the drive shaft and the driven shaft during operation. In some embodiments, the drive shaft, the lock, the driven rotor, the driven rotor retainer and the housing include plastic, wherein the plastic is disposable.

In another embodiment, the prophy angle includes a drive shaft configured to drive a non-orthogonal gear connection of the prophy angle. The drive shaft includes a distal end that is configured as a drive surface, a shaft positioning neck and a shaft tail; a drive shaft lock configured to lock the non-orthogonal gear connection of the prophy angle, the drive shaft lock including two lock legs with lock hooks; a driven rotor configured to rotate the non-orthogonal gear connection of the disposable dental prophy angle, the driven rotor including a rotor head, a rotor neck, a cam surface, a cup flange, and a cup holder.

In yet another embodiment, the prophy angle includes a drive shaft lock that is horseshoe-shaped and includes two lock legs with hooks. The lock legs are disposed perpendicular to the central axis of the longitudinal section of the housing. In one embodiment, there is a separation gap between the lock legs being greater than the diameter of the drive shaft neck. The drive shaft lock is permanently located through a slot in the housing, riding on the shaft positioning neck of the drive shaft to ensure a secure assembly and to prevent any backward motion of the drive shaft along the longitudinal axis.

Figure 11:
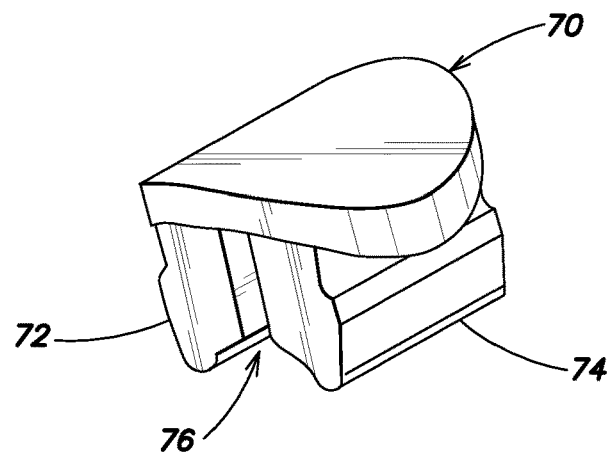
FIG. 11 illustrates a perspective view of an embodiment of a locking mechanism for a prophy angle dental device.
Figure 12:
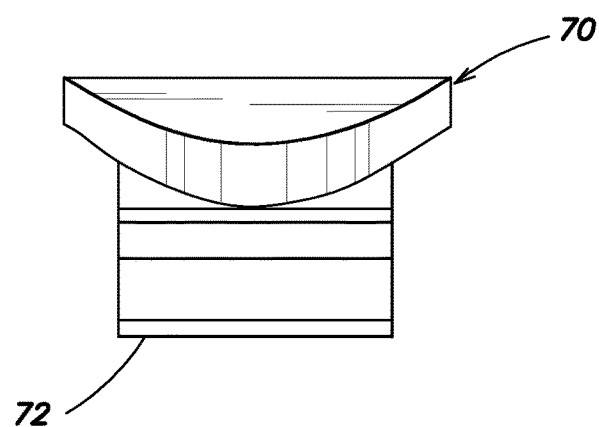
FIG. 12 illustrates a perspective view of an embodiment of a locking mechanism for a prophy angle dental device.

More particularly, in FIGS. 11 and 12, a lock 70 is configured for engagement with the drive shaft and housing 12. In some embodiments, lock 70 is horseshoe shaped and includes two lock legs 72, 74 configured to engage the drive shaft 24. In one embodiment, lock legs 72, 74 are perpendicular to driven shaft 30 and lock legs 72, 74 define a gap 76 configured to engage drive shaft 24 to prevent its rotation. Gap 76 includes a diameter larger than a diameter of the drive shaft 24. The lock 70 is configured to engage the drive shaft 24 by a pushing force and is movable in an unlocked position where it does not prevent rotation of the drive shaft 24 and a locked position where it engages the drive shaft 24 and prevents its rotation.

Figure 9:
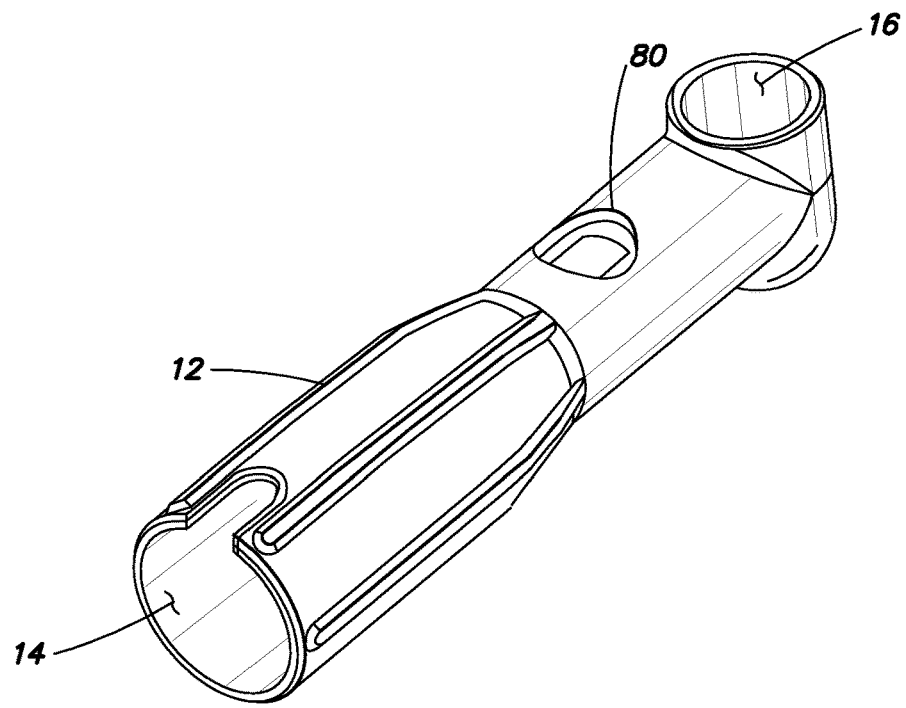
FIG. 9 illustrates a perspective view of a housing of a prophy angle dental device.

Housing 12 includes a slot 80 shown in FIG. 9 configured to receive lock 70. The first cavity 14 of the housing is configured to receive the drive shaft 24 and second cavity 16 of the housing is configured to receive driven shaft 30.

Figure 10:
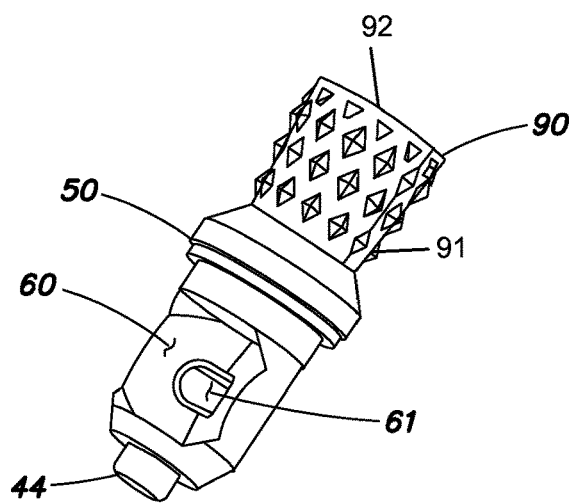
FIG. 10 illustrates a perspective view of a head of a prophy angle dental device.

FIG. 10 shows an enlarged view of the driven shaft cavity 61 that is configured to engage projection 28 of the drive shaft and cavity 60 has a corresponding shape to the conical portion 29 of the drive shaft. Rotor neck 44 can contact the housing at the second cavity 16, which also eases oscillation of the prophy cup 90. In some embodiments, the prophy cup comprises a plurality of dimples 91 disposed on the surface of the prophy cup that aid abrasion and dispersion of the dental paste as it contacts the teeth. The dental paste can be held in space 92 of the prophy cup 90. The prophy cup can be pressed against the teeth as the prophy cup oscillates back and forth.

Prophy cup 90 is configured for attachment to a prophy cup holder 50. In one embodiment, prophy cup 90 is overmolded directly onto a driven shaft, creating a monolithic part. This configuration removes the relative rotational motion and associated heat generation between the driven gear and prophy cup 90. This configuration improves polishing efficiency by reducing the downtime caused by excessive heat during procedures.

In one embodiment, there is a method of making a disposable prophy angle, the method comprising overmolding a prophy cup to a driven shaft of a housing, the housing containing a drive shaft and the driven shaft; the drive shaft having a proximal end and a distal end and a longitudinal axis therebetween, the distal end having a substantially conical driving portion and a projection, the proximal end of the drive shaft configured to engage a dental hand piece; and the driven shaft having a driven portion comprising a recess configured for engagement by the projection and/or the substantially conical portion of the drive shaft to oscillate the driven shaft at an oscillation angle greater than 90 degrees.

In one embodiment, as shown in FIGS. 13 and 14, a housing 112 includes a cavity 114 defining a longitudinal axis L3 and a cavity 116 defining a longitudinal axis L4. Axis L3 is disposed at an angle α greater than 90 degrees relative to axis L4. In this configuration, the drive shaft is disposed at an angle such that drive shaft 24 is disposed transverse to driven shaft 30.

As shown in FIG. 14, the angle α between drive shaft 24 and driven shaft 30 is non-orthogonal. In some embodiments, drive shaft 24 is disposed at an angle of 96 to 120 degrees relative to driven shaft 30. In some embodiments, drive shaft 24 is disposed at an angle of about 96, 97, 98, 99, 100, 101, 102, 103, 104, 105, 106, 107, 108, 109, 110, 111, 112, 113, 114, 115, 116, 117, 118, 119 to about 120 degrees relative to driven shaft 30. The connection of driven shaft 30 with a non-orthogonal gear connection facilitates tooth cleaning operations by allowing the dental prophy angle to ergonomically correct neutral wrist position.

In some embodiments, the prophy angle may have contours and allow easy grasping of the device during use. In various embodiments, the prophy angle is a contra angle that is angled for either a right handed or left handed user or angled to universally adapt to any hand, allowing the user to easily apply paste to the patient's teeth. In some embodiments, the prophy angle can be angled for either right or left hand users. In some embodiments, the prophy angle can be transparent so the user can see the position of the drive shaft and driven shaft or if the drive shaft is in a locked position or an unlocked position.

In some embodiments, a disposable prophy angle is provided comprising a housing containing a drive shaft and a driven shaft. The drive shaft having a proximal end and a distal end and a longitudinal axis therebetween. The distal end has a substantially conical driving portion and a projection. The proximal end of the drive shaft is configured to engage a dental hand piece. The driven shaft has a driven portion comprising a recess configured for engagement by the projection and/or the substantially conical portion of the drive shaft to oscillate the driven shaft at an oscillation angle greater than 90 degrees to about 120 degrees. The disposable prophy angle is a contra angle and a prophy cup is attached to the driven shaft by overmolding.

In some embodiments, the drive shaft, lock 70, driven rotor 40, a driven rotor retainer, and housings 12 and/or 112 comprise a plastic resin, wherein the plastic is disposable. In some embodiments, prophy angle 10 is non-disposable. In some embodiments, all or a portion of prophy angle 10 comprises at least one of stainless steel alloys, commercially pure titanium, titanium alloys, Grade 5 titanium, cobalt-chrome alloys, stainless steel alloys, calcium phosphate, polyaryletherketone (PAEK), polyetheretherketone (PEEK), polyetherketoneketone (PEKK), polyetherketone (PEK), or carbon-PEEK composites.

In various embodiments, all or a portion of prophy angle 10 may be made from materials, such as for example, polyurethane, polyurea, polyether(amide), PEBA, thermoplastic elastomeric olefin, copolyester, and styrenic thermoplastic elastomer, metal alloys with high non-ferrous metal content and a low relative proportion of iron, carbon fiber, glass fiber, plastics, ceramics or combinations thereof.

The prophy angle provided can be used in a method to apply a dental composition to a tooth structure, the method comprising applying a dental paste in a prophy cup to the tooth structure, the prophy cup attached to a driven shaft of a housing, the housing containing a drive shaft and the driven shaft; the drive shaft having a proximal end and a distal end and a longitudinal axis therebetween, the distal end having a substantially conical driving portion and a projection, the proximal end of the drive shaft configured to engage a dental hand piece; and the driven shaft having a driven portion comprising a recess configured for engagement by the projection and/or the substantially conical portion of the drive shaft to oscillate the driven shaft at an oscillation angle greater than 90 degrees. The dental composition can comprise a dental paste that polishes and cleans the teeth and can prevent tooth decay.

The dental paste can be applied to a tooth structure of a human patient (e.g., adults, children) or of a veterinary animal (dogs, cats, rabbits, rodents (e.g., hamsters, gerbils, mice, etc.), guinea pigs, ferrets, monkeys, horses, goats, cows, donkey, or the like).

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A disposable prophy angle comprising: a housing containing a drive shaft and a driven shaft; the drive shaft having a ring, a proximal end and a distal end and a longitudinal axis therebetween, the distal end having a substantially conical driving portion and a projection having a groove and a tapered surface extending from the groove toward the ring of the drive shift, the proximal end of the drive shaft configured to engage a dental hand piece; and the driven shaft having a driven portion comprising a recess configured for engagement by the projection and/or the substantially conical portion of the drive shaft to oscillate the driven shaft at an oscillation angle greater than 90 degrees.

2. A disposable prophy angle according to claim 1, wherein (i) the drive shaft causes the driven shaft to oscillate a various speeds, when the proximal end is connected to the dental hand piece; (ii) the disposable prophy angle reduces splatter of a dental paste; (iii) the disposable prophy angle reduces heat from contact friction between the drive shaft and the driven shaft; and/or (iv) the driven shaft oscillates laterally.

3. A disposable prophy angle according to claim 2, wherein (i) the drive shaft causes the driven shaft to oscillate at variable speeds of approximately 2500 to 6000 rpm and/or (ii) a prophy cup is attached to the driven shaft by overmolding.

4. A disposable prophy angle according to claim 1, wherein (i) the driven portion includes a cavity configured for disposal of the driving portion; (ii) the housing is angled for ease of the user; (iii) the driving portion is conical and has a diameter that is larger than the projection and the projection extends above the conical driving portion and both the conical driving portion and the projection engage the driven shaft; (iv) the distal end of the drive shaft comprises a diameter greater than the diameter of the proximal end of the drive shaft; (iv) the proximal end of the drive shaft extends out of the housing; or (v) a portion of the driven shaft extends out of the housing.

5. A disposable prophy angle according to claim 4, wherein the projection is configured to engage a portion of the cavity and facilitate oscillation of the driven shaft.

6. A disposable prophy angle according to claim 1, wherein the projection extends beyond a top surface of the conical portion.

7. A disposable prophy angle according to claim 1, wherein the drive shaft is disposed at an angle of about 96 degrees to about 120 degrees relative to the driven shaft.

8. A disposable prophy angle according to claim 1, further including a lock configured for engagement with the drive shaft and the housing.

9. A disposable prophy angle according to claim 8, wherein the lock is horseshoe shape including two lock legs configured for disposal of the drive shaft.

10. A disposable prophy angle according to claim 9, wherein the two lock legs are perpendicular to the driven shaft and the legs define a gap having a diameter larger than a diameter of the drive shaft.

11. A disposable prophy angle according to claim 1, wherein the housing includes a slot configured to receive a locking mechanism.

12. A disposable prophy angle according to claim 1, wherein the projection extends along an axis of the drive shaft.

13. A disposable prophy angle according to claim 1, wherein the projection includes a tapered diameter.

14. A disposable prophy angle according to claim 1, wherein the drive shaft is disposed transverse to the driven shaft.

15. A disposable prophy angle according to claim 1, wherein the driven shaft includes a connection for disposal of a prophy cup.

16. A disposable prophy angle according to claim 1, wherein the driven shaft includes a connection to a prophy cup and is configured to oscillate the prophy cup at a variable speed.

17. A disposable prophy angle according to claim 1, wherein the drive shaft is disposed at an angle greater than 90 degrees to the driven shaft.

18. A disposable prophy angle according to claim 1, wherein the drive shaft includes a groove disposed along a longitudinal axis of the drive shaft.

19. A disposable prophy angle according to claim 1, wherein the drive shaft includes a groove disposed along a longitudinal axis of the drive shaft, wherein the groove includes a tapered diameter.

20. A disposable prophy angle comprising: a housing containing a drive shaft and a driven shaft; the drive shaft having a proximal end and a distal end and a longitudinal axis therebetween, the distal end having a substantially conical driving portion and a projection extending along the longitudinal axis of the conical driving portion, the projection having a groove and a tapered surface, the proximal end of the drive shaft configured to engage a dental hand piece; the driven shaft having a driven portion comprising a recess configured for engagement by the projection and/or the substantially conical portion of the drive shaft so as to oscillate the driven shaft at an oscillation angle of about 120 degrees; and a prophy cup contacting the driven shaft to oscillate with the driven shaft.

21. A disposable prophy angle according to claim 20, wherein the projection includes a tapered diameter.

22. A disposable prophy angle according to claim 20, wherein the drive shaft is disposed transverse to the driven shaft.

23. A disposable prophy angle comprising: a housing containing a drive shaft and a driven shaft; the drive shaft having a proximal end and a distal end and a longitudinal axis therebetween, the distal end having a substantially conical driving portion and a projection extending along the longitudinal axis of the driving portion, the projection having a groove and a tapered surface, the proximal end of the drive shaft configured to engage a dental hand piece; the driven shaft having a driven portion comprising a recess configured for engagement by the projection and/or substantially conical portion of the drive shaft so as to oscillate the driven shaft at an oscillation angle of about 120 degrees; and a prophy cup contacting the driven shaft to oscillate with the driven shaft, wherein the drive shaft is disposed at an angle of about 96 degrees to about 120 degrees relative to the driven shaft.

24. A method of making a disposable prophy angle, the method comprising overmolding a prophy cup to a driven shaft of a housing, the housing containing a drive shaft and the driven shaft; the drive shaft having a proximal end and a distal end and a longitudinal axis therebetween, the distal end having a substantially conical driving portion and a projection having a groove and a tapered surface, the proximal end of the drive shaft configured to engage a dental hand piece; and the driven shaft having a driven portion comprising a recess configured for engagement by the projection and/or the substantially conical portion of the drive shaft to oscillate the driven shaft at an oscillation angle greater than 90 degrees.

25. A method according to claim 24, wherein the drive shaft is disposed at an angle of about 96 degrees to about 120 degrees relative to the driven shaft.

26. A method of applying a dental composition to a tooth structure, the method comprising applying a dental paste in a prophy cup to the tooth structure, the prophy cup attached to a driven shaft of a housing, the housing containing a drive shaft and the driven shaft; the drive shaft having a proximal end and a distal end and a longitudinal axis therebetween, the distal end having a substantially conical driving portion and a projection, the conical portion being adjacent to the projection, the proximal end of the drive shaft configured to engage a dental hand piece; and the driven shaft having a driven portion comprising a recess configured for engagement by the projection and/or the substantially conical portion of the drive shaft to oscillate the driven shaft at an oscillation angle greater than 90 degrees.

27. A method according to claim 26, wherein the tooth structure is in a veterinary animal.

28. A method according to claim 26, wherein the dental composition comprises a dental paste that polishes and cleans the teeth.

29. A method according to claim 26, wherein the dental composition is used to prevent tooth decay.

* * * * *